(12) United States Patent
Marti et al.

(10) Patent No.: US 7,348,361 B2
(45) Date of Patent: Mar. 25, 2008

(54) SOLUTION FOR DIAGNOSING OR TREATING TISSUE PATHOLOGIES

(75) Inventors: Alexandre Marti, Geneva (CH); Norbert Lange, Lausanne (CH); Matthieu Zellweger, Lausanne (CH); Georges Wagnieres, Morges (CH); Hubert Van Den Bergh, Goumoens-la-Ville (CH); Patrice Jichlinski, Le Mont-sur-Lausanne (CH); Pavel Kucera, Lausanne (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 0 days.

(21) Appl. No.: 09/673,871

(22) PCT Filed: Apr. 22, 1999

(86) PCT No.: PCT/CH99/00163

§ 371 (c)(1),
(2), (4) Date: Nov. 30, 2000

(87) PCT Pub. No.: WO99/53962

PCT Pub. Date: Oct. 28, 1999

(65) Prior Publication Data

US 2003/0158258 A1 Aug. 21, 2003

(30) Foreign Application Priority Data

Apr. 22, 1998 (FR) .................... 98 05425

(51) Int. Cl.
*A61K 31/195* (2006.01)
*A61K 49/00* (2006.01)
*A61K 31/40* (2006.01)
*A01N 43/38* (2006.01)

(52) U.S. Cl. ............... 514/561; 514/410; 424/9.61
(58) Field of Classification Search ........... 514/410, 514/561, 814, 146; 424/9.61
See application file for complete search history.

(56) References Cited

U.S. PATENT DOCUMENTS 5,234,940 A * 8/1993 Kennedy .................. 514/410
5,856,566 A * 1/1999 Golub ...................... 562/567
5,955,490 A * 9/1999 Kennedy .................. 514/410
6,034,267 A * 3/2000 Gierskcky et al. ....... 560/155

FOREIGN PATENT DOCUMENTS

WO WO 96/28412 9/1996

OTHER PUBLICATIONS

Callewaert et al, Basic Chemistry, Worth Publisher, Inc. p. 420-421, 1980.*
PDR Electronic Library™ 2003: see Description under the product Desferal, p. 1/9.*
*Journal of Photochemistry and Photobiology B and Biology*, Fin-Puches et al, "Primary Clinical Response and Long-Term Follow-Up of Soloar Keratoses Treated with Topically Applied 5-Aminolevulinic-Acid and Irradiation by Different Wave Bands of Light", vol. 41, 1997.
"The Efficacy of an Iron Chelator (CP94) in Increasing Cellular Protoporphyrin IX Following Intravestical 5-Aminolaevulinic Acid Administration: An In Vivo Study" by Chang et al, Apr. 1997, SWITZERLAND.
*Nouvelles Dermatologigues [Dermatology News]*. P. Thomas, "Phototherapie Dynamique Topique". ["Dynamic Topical Phototherapy"], 1996, France.
K. Svanberg et al., "Photodynamic therapy of non-melanoma malignant tumours of the skin using topical 5-amino levulinic acid sensitization and laser irradiation," British Journal of Dermatology (1994) vol. 130, pp. 743-751.
R. Bachor et al., "Photodynamic Therapy using Aminolevulinic Acid (ALA)," Univ. of Ulm, Dept. of Urology, 7900 Ulm, Germany, SPIE, vol. 2078, pp. 372-380.
C. Abels, "In vivo kinetics and spectra of 5-aminolaevulinic acid-induced fluorescence in an amelanotic melanoma of the hamster, "British Journal Cancer (1994), vol. 70, pp. 826-833.

* cited by examiner

*Primary Examiner*—Sreeni Padmanabhan
*Assistant Examiner*—Yong S. Chong
(74) *Attorney, Agent, or Firm*—Kenyon & Kenyon LLP

(57) ABSTRACT

The invention concerns a 5-aminolevulinic acid ester (E-ALA) solution for producing a pharmaceutical preparation useful for diagnosing and/or treating tissue and/or cell pathologies by local radiation exposure using radiation emitted by a light source energy followed, in the case diagnosis, by detection of fluorescent protoporphyrin IX (Pp1X). The E-ALA concentration in the solution is less than 1% and ranges between 0.01% and 0.5%. The low E-ALA concentration in the solution increases Pp1X synthesis and homogenises its distribution in the cell layers while highly reducing the secondary toxicity for the treated cells.

31 Claims, No Drawings

SOLUTION FOR DIAGNOSING OR TREATING TISSUE PATHOLOGIES

TECHNICAL REALM

The present invention concerns a 5-aminolevulinic acid ester (E-ALA) for producing a pharmaceutical preparation used in the diagnosis and treatment of tissue and/or cellular pathologies by local radiation exposure using radiation emitted by a light source followed, in the case of diagnosis, by detection of fluorescence emitted by the substances for which the 5-aminolevulinic acid ester (ALA) or the E-ALA are precursors, particularly protoporphyrin IX (PpIX).

PRIOR ART

The use of compounds for which ALA or ALA esters (E-ALA) and particularly hexylester hydrochloric ALA (h-ALA) are precursors is well known in the diagnosis and/or treatment of lesions, particularly cancerous lesions. This principle is thoroughly discussed in patent Publication No. WO 96/28412. The solution may be administered orally or parenterally, for example, by intra-dermal, subcutaneous, intra-peritoneal or intravenous injection. It may also be administered topically, for example locally, by exposing the surface of the organ to be treated to an E-ALA or ALA solution. A pad saturated with such a solution can also be used during topical administration. The concentration of the ALA (E-ALA) ester solution mentioned in this publication ranges from 1 to 50% and preferably between 15% and 30%. However, this concentration generates essentially no PpIX in certain organs which are principally involved in this type of treatment, namely the bladder.

In the publications in the *Journal of Photochemistry and Photobiology B and Biology*, respectively, by Fin-Puches et al entitled "Primary Clinical Response and Long-Term Follow-Up of Solar Keratoses Treated with Topically Applied 5-Aminolevulinic Acid and Irradiation by Different Wave Bands of Light," and by Chang et al entitled "The Efficacy of an Iron Chelator (CP94) in Increasing Cellular Protoporphyrin IX Following Intravestical 5-Aminolaevulinic Acid Administration: An In Vivo Study," as well as the article in *Nouvelles Dermatologiques [Dermatology News]* by P. Thomas entitled "Photothérapie Dynamique Topique" ["Dynamic Topical Phototherapy"], the product used in treatment is ALA and not an ALA ester, which vary greatly in concentration. The ALA concentrations used are actually a minimum of 45 to 60 times higher than what is required when using an ALA ester solution (E-ALA).

Administering this substance in such strong concentrations has proven toxic to human tissue in certain instances. This toxicity, present even in the absence of light source radiation, can seriously deter generation of protoporphyrin IX (PpIX). For this reason, such concentrations either cannot be used in certain cases or are not ideal for the detection and treatment of lesions.

Furthermore, the time required to activate the active principles induced by the medicated solution is extremely long if free 5-aminolevulinic acid, that is, non-esterized ALA, is used. For this reason diagnosis and treatment using free ALA can only take place in a hospital setting, since the patient must frequently be immobilized for a very long period of time, approximately 5 hours.

In a climate where the cost of medical care is generally being reduced and preference is given to home health care, office treatment or one-day hospital care, the current treatment procedures are not only burdensome and restrictive for the patient, but costly to health insurance companies and the community.

Despite the technological progress which the use of ALA or E-ALA has contributed in terms of early diagnosis and effective treatment of certain afflictions, there are some major obstacles to its widespread use.

DESCRIPTION OF THE INVENTION

The goal of the present invention is to overcome these obstacles through the use of a solution designed for the diagnosis and/or treatment of cancerous lesions, particularly in the field of urology, administered in concentrations that will not prejudice biosynthesis of the active compounds and which is demonstrably very effective when applied for relatively short periods of time, making it appropriate for use in one-day clinics or even doctors' offices. Specifically, this solution must foster strong PpIX accumulation over a minimum time period and very thorough PpIX distribution throughout the treated tissue.

This goal is achieved using a 5-aminolevulinic acid ester (E-ALA) such as that defined in the preamble, characterized in that the concentration C of E-ALA in the solution is less than 1% and ranges from 0.01% to 0.5% ($0.01\% \leq C \leq 0.5\%$).

It has been shown in practice that use of a very low concentration of E-ALA in the solution increases PpIX synthesis and homogenizes distribution throughout the cellular layers, while at the same time greatly reducing secondary toxicity of the solution to the treated cells. This becomes even more important because when treating a tumor with dynamic phototherapy, the rapid photobleaching reduces PpIX concentration; complete destruction of the tumor implies an elevated initial accumulation of intracellular PpIX and thorough distribution throughout the layers of the tumor.

Advantageously, the ALA (E-ALA) ester producing the best results is hexylester hydrochloride ALA (h-ALA).

The solution is preferably produced by dissolving the ALA (E-ALA) ester in a solvent compatible with human or animal organisms.

Said solvent is advantageously selected from the following substances: sterilized filtered water, physiological NaCl solution, phosphate buffer solutions, with phosphate, or alcohol.

In its preferred form, the solution comprises a component for adjusting the PH to a physiological value ranging from 4.8 to 8.1.

In an advantageous form, the solution may comprise a complementary substance to prevent the transformation of the PpIX into a heme by iron complexing in the living cells.

Said complementary substance may be an EDTA (ethylene diamine tetmacetate) or deferoxamine mesylate (DESFERAL).

PREFERRED EMBODIMENT OF THE INVENTION

The present invention will be better understood with reference to the following description of a preferred embodiment of the solution according to the invention and its variations, and by way of illustration, a particularly advantageous application of the solution in the diagnosis and/or treatment of lesions inside a cavity in a human or animal organism, such as the bladder.

A 5-aminolevulinic acid solution (E-ALA) is prepared by dissolving said substance, which may be an amorphous powder or in crystalline form, in an appropriate solvent compatible with in vivo use. By way of example, this solution may consist of sterilized demineralized water, physiological NaCl solution containing approximately 9% NaCl, a phosphate buffer solution, an alcohol, or a solution containing alcohol or the like.

The solution can be completed by the addition of a complementary substance to prevent the PpIX from transforming into a heme by iron complexing in the living cells. This complementary substance may be an EDTA (ethylene diamine tetraacetate) or deferoxamine mesylate (DESFERAL).

The solution can be completed by the addition of a complementary substance to prevent the PpIX from transforming into a heme by iron complexing in the living cells. This complementary substance may be an EDTA (tetra acetate diaminoethyl), deferoxamine or desferal.

One especially interesting application is the diagnosis and treatment of cancerous lesions in the field of urology, particularly on the interior bladder walls.

According to one application, the solution may be administered topically, contacting the interior walls of the organ. The bladder is filled with about 50 ml of low concentration ALA (E-ALA) ester or ALA (h-ALA) hexylester solution, e.g., a concentration C (by weight) ranging from 0.01% and 0.5% and preferably equal to 0.2%.

Instillation may last from ½ hour to 7 hours, but preferably ranges from ½ hour to 4 hours.

Surprisingly, it has been noted that with the use of these low concentrations which differ considerably from the 15 to 30% concentrations currently used in this field, the ALA (E-ALA) ester is more effective, as measured by an increased presence of fluorescent protoporphyrin IX (PpIX) apparent at the location of the lesions on the interior bladder walls and improved protoporphyrin distribution in the cell layers. Furthermore, due to these low concentrations, cytotoxicity is reduced, which considerably decreases the risk of undesirable secondary effects. In particular, this reduced cytotoxicity favors the generation of the light sensitive and/or fluorescent substances to which free E-ALA or ALA are the precursors. Moreover, generating maximum PpIX shortens the time elapsing between administering the solution and performing the actual intervention.

One variation in application is defined as "fractionated topical method." It may comprise the following steps:

a first bladder instillation lasting from ½ hour to 3 hours, and preferably lasting for about 2 hours;

rinsing the bladder;

a second instillation lasting from ½ hour to 3 hours, and preferably lasting for about 2 hours;

rinsing the bladder.

After a waiting period of from 0 to 4 hours, and preferably for about 2 hours, fluorescent treatment and detection of the bladder can take place.

Topical solution of the ALA (E-ALA) ester solution or the ALA (h-ALA) hexylester solution may also be replaced by systemic application. In this case, the solution is administered either orally or parenterally either alone or in combination with compounds known as transporters, such as, for example, dimethylsulfoxide, glycine or the like, to enhance absorption and/or migration of the active substance, with the occurrence of the ALA (E-ALA) ester or the ALA (h-ALA) hexylester through the tissues and/or cells.

Finally, a way to activate penetration of the ALA (E-ALA) ester or the ALA (h-ALA) hexylester into the tissue or cells may consist of forming an iontophoresis on the walls of the organ concerned.

These phases are followed by one or more phototherapy and/or fluorescent treatment phases.

During phototherapy treatment, the walls of the organ concerned (for example, the bladder) are irradiated with a light beam called the excitant light, which may or may not be monochromatic, either continuously or sequentially, preferably situated in the spectrum domain ranging from 300 to 900 nanometers and preferably between 350 and 650 nanometers.

During phototherapy proceedings the lighting E applied to the bladder walls, which is light power per surface unit, ranges from 0.1 mW/cm$^2$ to 1 W/cm$^2$, and preferably between 5 mW/cm$^2$ and 500 mW/cm$^2$. This light induces a phototoxic reaction due to the presence of protoporphyrin IX (PpIX) in particular and/or its photo-products in the tissue. The light doses may be applied homogeneously over the entire wall of the organ, or selectively at only the locations that have been identified as having lesions. During fluorescent diagnosis, the bladder walls are irradiated using a beam with a spectral width ranging from 300 to 700 nanometers, and preferably from 350 to 650 nanometers. For these fluorescent diagnoses, the lighting E applied to the bladder walls (light power per surface unit) ranges from 1 mW/cm$^2$ and 1 mW/cm$^2$ and preferably between 50 mW/cm$^2$ to 500 mW/cm$^2$. The excitant light induces fluorescence in the substances to which E-ALA and especially h-ALA are precursors, particularly PpIX. This fluorescence is collected by an optical system and detected visually or by a specific, linear or matric detector such as a camera.

In addition to the advantages outlined above, the use of solutions with low ALA ester concentrations provides an inexpensive product for use in either phototherapy treatment or photodetection, at low production cost and with simplified Galenic pharmaceuticals.

The invention claimed is:

1. A pharmaceutical preparation to be administered to a patient for at least one of diagnosis and treatment of tissue or a cell lesion followed by localized irradiation using a beam emitted by a source of light energy, the pharmaceutical preparation comprising:

a physiologically acceptable solvent; and

ALA hexylester (h-ALA) for generating protoporphyrin IX (PpIX) which is present in the pharmaceutical preparation at a concentration of less than 1% by weight.

2. The pharmaceutical preparation according to claim 1, wherein the ALA hexylester (h-ALA) is dissolved in a solvent which is compatible with a human organism.

3. The pharmaceutical preparation according to claim 2, wherein the solvent is selected from the group consisting of sterilized water, physiological NaCl solution, and a phosphate buffer solution.

4. The pharmaceutical preparation according to claim 2, wherein the pharmaceutical preparation contains a component to adjust the pH of the pharmaceutical preparation to a physiological value ranging from about 4.8 to about 8.1.

5. The pharmaceutical preparation according to claim 1, wherein the pharmaceutical preparation comprises a complementary substance for preventing transformation of the protoporphyrin IX (PpIX) into a heme by iron complexing in the cells.

6. The pharmaceutical preparation according to claim 5, wherein the complementary substance is ethylene diamine tetraacetate (EDTA).

7. The pharmaceutical preparation according to claim 5, wherein the complementary substance is deferoxamine mesylate.

8. The pharmaceutical preparation according to claim 1, wherein the ALA hexylester (h-ALA) is dissolved in a solvent which is compatible with an animal organism.

9. The pharmaceutical preparation according to claim 8, wherein the solvent is selected from the group consisting of sterilized water, physiological NaCl solution, and a phosphate buffer solution.

10. The pharmaceutical preparation according to claim 8, wherein the pharmaceutical preparation contains a component to adjust the pH of the pharmaceutical preparation to a physiological value ranging from about 4.8 to about 8.1.

11. The pharmaceutical preparation according to claim 1, wherein, following administration of the pharmaceutical preparation to the patient and irradiation of the tissue or the cell lesion by the source of light energy, a fluorescence emitted by protoporphyrin IX (PpIX) generated by the ALA hexylester (h-ALA) contained in the pharmaceutical preparation is detected to facilitate diagnosis of the tissue or the cell lesion.

12. A pharmaceutical preparation to be administered to a patient for at least one of diagnosis and treatment of tissue or a cell lesion followed by localized irradiation using a beam emitted by a source of light energy, the pharmaceutical preparation comprising:
   a physiologically acceptable solvent;
   ALA hexylester (h-ALA) for generating protoporphyrin IX (PpIX) which is dissolved in the solvent at a concentration of less than 1% by weight;
   a pH in the range of from about 4.8 to about 8.1; and
   a complementary substance for preventing transformation of protoporphyrin IX (PpIX) into a heme by iron complexing in live cells, the complementary substance selected from ethylene diamine tetraacetate (BDTA), and deferoxamine mesylate.

13. The pharmaceutical preparation according to claim 12, wherein, following administering the pharmaceutical preparation to the patient and irradiation of the tissue or the cell lesion by the source of light energy, a fluorescence emitted by protoporphyrin IX (PpIX) generated by the ALA hexylester (h-ALA) contained in the pharmaceutical preparation is detected to facilitate diagnosis of the tissue or the cell lesion.

14. A method of diagnosis of a tissue or a cell lesion in an organism, said method comprising:
   (a) administering to the organism the pharmaceutical preparation of claim 1
   (b) irradiating the tissue or the cell lesion with a source of light energy; and
   (c) detecting fluorescence emitted by protoporphyrin IX (PpIX) generated by the ALA hexylester (h-ALA).

15. The method of claim 14, wherein the concentration of the ALA hexylester (h-ALA) in the pharmaceutical preparation ranges from 0.01% by weight to 0.5% by weight.

16. The method of claim 14, wherein the solvent is selected from the group consisting of sterilized water, physiological NaCl solution, and a phosphate buffer solution.

17. The method of claim 14, wherein the pharmaceutical preparation contains a component to adjust the pH of the pharmaceutical preparation to a physiological value ranging from about 4.8 to about 8.1.

18. The method of claim 14, wherein the pharmaceutical preparation comprises a complementary substance for preventing transformation of the protoporphyrin IX (PpIX) into a heme by iron complexing in the cells.

19. The method of claim 18, wherein the complementary substance is ethylene diamine tetraacetate (EDTA).

20. The method of claim 18, wherein the complementary substance is deferoxamine mesylate.

21. The method of claim 14, wherein the organism is a human or an animal.

22. A method of treatment of a tissue or a cell lesion in an organism, said method comprising:
   (a) administering to the organism a the pharmaceutical preparation of claim 1; and
   (b) irradiating the tissue or the cell lesion with a source of light energy.

23. The method of claim 22, wherein the concentration of the ALA hexylester (h-ALA) in the pharmaceutical preparation ranges from 0.01% by weight to 0.5% by weight.

24. The method of claim 22, wherein the solvent is selected from the group consisting of sterilized water, physiological NaCl solution, and a phosphate buffer solution.

25. The method of claim 22, wherein the pharmaceutical preparation contains a component to adjust the pH of the solution to a physiological value ranging from about 4.8 to about 8.1.

26. The method of claim 22, wherein the pharmaceutical preparation comprises a complementary substance for preventing transformation of the protoporphyrin IX (PpIX) into a heme by iron complexing in the cells.

27. The method of claim 26, wherein the complementary substance is ethylene diamine tetraacetate (EDTA).

28. The method of claim 26, wherein the complementary substance is deferoxamine mesylate.

29. The method of claim 22, wherein the organism is a human or an animal.

30. The pharmaceutical preparation of claim 19, wherein the concentration of the ALA hexylester (h-ALA) ranges from 0.01% by weight to 0.5% by weight.

31. The pharmaceutical preparation of claim 12, wherein the concentration of the ALA hexylester (h-ALA) ranges from 0.01% by weight to 0.5% by weight.

* * * * *

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 7,348,361 |
| (45) | ISSUED | : | March 25, 2008 |
| (75) | INVENTOR | : | Alexandre Marti et al. |
| (73) | PATENT OWNER | : | Norbert Lange; École Polytechnique Fédérale de Lausanne and University of Lausanne |
| (95) | PRODUCT | : | CYSVIEW® (hexaminolevulinate hydrochloride) |

This is to certify that an application under 35 U.S.C. § 156 has been filed in the United States Patent and Trademark Office, requesting extension of the term of U.S. Patent No. 7,348,361 based upon the regulatory review of the product CYSVIEW® (hexaminolevulinate hydrochloride) by the Food and Drug Administration. Since it appears that the requirements of the law have been met, this certificate extends the term of the patent for the period of

(94)                                564 days from April 22, 2019, the original expiration date of the patent, subject to the payment of maintenance fees as provided by law, with all rights pertaining thereto as provided by 35 U.S.C. § 156.

I have caused the seal of the United States Patent and Trademark Office to be affixed this 30th day of January 2014.

Michelle K. Lee
Deputy Under Secretary of Commerce for Intellectual Property and
Deputy Director of the United States Patent and Trademark Office